(12) United States Patent
Moon et al.

(10) Patent No.: US 9,777,282 B2
(45) Date of Patent: Oct. 3, 2017

(54) *CORYNEBACTERIUM* MICROORGANISM WITH IMPROVED ABILITY TO PRODUCE L-LYSINE AND METHOD FOR PRODUCING L-LYSINE USING THE SAME

(71) Applicant: CJ CHEILJEDANG CORPORATION, Seoul (KR)

(72) Inventors: Jun Ok Moon, Seoul (KR); Sang Hee Park, Seoul (KR); Lan Huh, Seoul (KR); Kwang Ho Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/103,147

(22) PCT Filed: Dec. 8, 2014

(86) PCT No.: PCT/KR2014/011984
§ 371 (c)(1),
(2) Date: Jun. 9, 2016

(87) PCT Pub. No.: WO2015/088204
PCT Pub. Date: Jun. 18, 2015

(65) Prior Publication Data
US 2016/0355830 A1    Dec. 8, 2016

(30) Foreign Application Priority Data
Dec. 13, 2013  (KR) .................. 10-2013-0155634

(51) Int. Cl.
*C12P 13/08* (2006.01)
*C07K 14/34* (2006.01)
*C12N 15/77* (2006.01)
*C12N 1/21* (2006.01)
*C12R 1/15* (2006.01)

(52) U.S. Cl.
CPC .............. *C12N 15/77* (2013.01); *C07K 14/34* (2013.01); *C12P 13/08* (2013.01); *C12R 1/15* (2013.01)

(58) Field of Classification Search
None
See application file for complete search history.

(56) References Cited

U.S. PATENT DOCUMENTS

| | | | |
|---|---|---|---|
| 6,962,989 B1 | 11/2005 | Pompejus et al. | |
| 7,160,704 B2 | 1/2007 | Takeshita et al. | |
| 7,794,990 B2 | 9/2010 | Park et al. | |
| 2002/0107377 A1* | 8/2002 | Farwick | C07K 14/34 536/23.2 |
| 2003/0087400 A1 | 5/2003 | Mockel et al. | |
| 2009/0029356 A1 | 1/2009 | Pompejus et al. | |

FOREIGN PATENT DOCUMENTS

| | | |
|---|---|---|
| EP | 1108790 A2 | 6/2001 |
| EP | 2298880 A1 | 3/2011 |
| JP | 2001178481 A | 7/2001 |
| KR | 1020070056807 A | 6/2007 |
| RU | 2333247 C2 | 8/2005 |
| WO | 0222670 A1 | 3/2002 |

OTHER PUBLICATIONS

Donovan et al., Cell division in Corynebacterineae, Frontiers Microbiol., 2014, 5, 1-16.*
Valbuena et al., Morphological changes and proteome response of Corynebacterium glutamicum to a partial depletion of FtsI, Microbiol., 2006, 152, 2491-2503.*
Letek et al., Characterization of the promoter region of ftsZ from Corynebacterium glutamicum and controlled overexpression of FtsZ, Int. Microbiol., 2007, 10, 271-82.*
Hartmann et al., Identification and characterization of the last two unknown genes, dapC and dapF, in the succinylase branch of the L-lysine biosynthesis of Corynebacterium glutamicum, J. Biotech., 2003, 104, 199-211.*
Uniprot, Accession No. Q8NRSO, 2013, www.uniprot.org.*
Geissler et al., Evidence for functional overlap among multiple bacterial cell division proteins: compensating for the loss of FtsK, Mol. Microbiol., 2005, 58, 569-612.*
XP-002770259] C. glutamicum marker and fine chemical production protein SEQ ID:1658., Database Geneseq, (Apr. 2, 2009), Database accession No. AWF57484, 2009.*
Bastian Blombach et al., Acetohydroxyacid Synthase, a Novel Target for Improvement of L-Lysine Production by Corynebacterium glutamicum, Applied and Environmental Microbiology, vol. 75(2), pp. 419-427(2009).
Bastian Blombach et al., Effect of pyruvate dehydrogenase complex deficiency on L-lysine production with Corynebacterium glutamicum, Appl Microbiol Biotechnol, vol. 76, pp. 615-623(2007).
Chang-Soo Lee et al., Next-Generation Sequencing-Based Genome-Wide Mutation Analysis of L-Lysine-Producing Corynebacterium glutamicum ATCC 21300 Strain, The Journal of Microbiology, vol. 50(5), pp. 860-863(2012).
International Search Report with English Translation for International Application No. PCT/KR2014/011984 dated Feb. 27, 2015.
Verena Engels et al., The Global Repressor SugR Controls Expression of Genes of Glycolysis and of the L-Lactate Dehydrogenase LdhA in Corynebacterium glutamicum, Journal of Bacteriology, vol. 190(24), pp. 8033-8044(2008).
Written Opinion for International Application No. PCT/KR2014/011984 dated Feb. 27, 2015.
Extended European Search Report for Application No. 14870476.0 dated May 29, 2017.
Elke E. E. Noens, et al., "FtsX and FtsE import autolytically produced peptidoglycan subunits during sporulation-specific cell division in Streptomyces coelicolor", 2007, pp. 1-192, Chapter 6.
Ramos Angelina et al., Altered morphology produced by ftsZ expression in Corynebacterium glutamicum ATCC 13869, 2005, p. 2563-2572, vol. 151, Microbiology.

* cited by examiner

*Primary Examiner* — Tekchand Saidha
*Assistant Examiner* — Todd M Epstein
(74) *Attorney, Agent, or Firm* — Cantor Colburn LLP

(57) ABSTRACT

A microorganism of the genus *Corynebacterium* with an improved ability to produce L-lysine in which a septum formation initiator protein is inactivated and a method for producing L-lysine using the microorganism.

4 Claims, No Drawings

SEQUENCE LISTING

```
<160> NUMBER OF SEQ ID NOS: 14

<210> SEQ ID NO 1
<211> LENGTH: 180
<212> TYPE: PRT
<213> ORGANISM: Coynebacterium

<400> SEQUENCE: 1

Met Ala Lys Gln Lys Lys Thr His Lys Gly Leu Val Pro Val Ser Ser
 1               5                  10                  15

Arg Glu Arg Ala Ser Glu Ser Val Ser Ala Thr Arg Ala Pro Phe Arg
                20                  25                  30

Leu Gly Ala Val Gly Ile Gly Ala Ile Ala Leu Val Val Leu Leu Ile
            35                  40                  45

Leu Phe Val Ile Ala Ile Pro Val Arg Asn Tyr Phe Gln Leu Arg Ser
        50                  55                  60

Asp Ile Ala Gln Thr Glu Ala Ser Ile Glu Ala Lys Glu Gln Gln Ile
 65                  70                  75                  80

Lys Gln Leu Glu Ser Asp Leu Asn Arg Tyr Gln Ser Glu Ala Tyr Ile
                85                  90                  95

Arg Glu Gln Ala Arg Leu Arg Leu Gly Val Ile Glu Pro Gly Glu Thr
            100                 105                 110

Ala Phe Arg Ile Val Asp Pro Ala Leu Asp Thr Asp Thr Ser Val Thr
        115                 120                 125

Ser Asp Gly Asn Glu Glu Lys Pro Leu Gly Ala Trp Tyr Glu Asn Leu
    130                 135                 140

Trp Asp Ser Val Thr Lys Pro Glu Ala Leu Gly Glu Glu Ile Ala
145                 150                 155                 160

Pro Pro Ala Val Glu Gly Glu Val Pro Thr Leu Ala Pro Thr Glu Glu
                165                 170                 175

Ala Thr Val Gln
            180

<210> SEQ ID NO 2
<211> LENGTH: 543
<212> TYPE: DNA
<213> ORGANISM: Corynebacterium

<400> SEQUENCE: 2
atggcaaagc agaagaaaac tcataaaggc cttgttcctg tctcaagcag ggaacgtgct      60
tcagagtcag tttctgctac ccgcgcccca tttagattgg gtgccgtcgg catcggtgca     120
atcgcactcg tagttcttct catcctgttt gtcatcgcga ttcctgtgcg taactatttt     180
cagctgcgct ccgacatcgc ccaaacagag gcttccattg aagccaaaga acaacagatc     240
aaacaactgg aatctgacct caacaggtac caatcagagg cgtacatccg cgaacaagca     300
cgcctgcgcc taggcgtcat tgaacctgga gaaaccgcgt tcagaatcgt ggacccagca     360
ctagataccg acacctcagt cacctctgac ggcaacgaag agaaaccact gggagcttgg     420
tatgaaaacc tctgggactc agtcaccaag ccagaagcac tcggcgaaga ggaaattgcg     480
```

-continued cctccagcag ttgagggaga agttccaaca cttgcaccaa ctgaggaagc aactgtgcaa    540
tag    543

<210> SEQ ID NO 3
<211> LENGTH: 44
<212> TYPE: PRT
<213> ORGANISM: Artificial Sequence
<220> FEATURE:
<223> OTHER INFORMATION: variant of pdz-ftsB

<400> SEQUENCE: 3

Met Ala Lys Gln Lys Lys Thr His Lys Gly Leu Val Pro Val Ser Ser
1               5                   10                  15

Arg Glu Arg Glu Glu Glu Ile Ala Pro Pro Ala Val Glu Gly Glu Val
            20                  25                  30

Pro Thr Leu Ala Pro Thr Glu Glu Ala Thr Val Gln
        35                  40

<210> SEQ ID NO 4
<211> LENGTH: 135
<212> TYPE: DNA
<213> ORGANISM: Artificial Sequence
<220> FEATURE:
<223> OTHER INFORMATION: variant of pdz-ftsB

<400> SEQUENCE: 4
atggcaaagc agaagaaaac tcataaaggc cttgttcctg tctcaagcag ggaacgtgaa    60
gaggaaattg cgcctccagc agttgaggga gaagttccaa cacttgcacc aactgaggaa    120
gcaactgtgc aatag    135

<210> SEQ ID NO 5
<211> LENGTH: 139
<212> TYPE: PRT
<213> ORGANISM: Artificial Sequence
<220> FEATURE:
<223> OTHER INFORMATION: variant of pdz-ftsB

<400> SEQUENCE: 5

Met Ala Lys Gln Lys Lys Thr His Lys Gly Leu Val Pro Val Ser Ser
1               5                   10                  15

Arg Glu Arg Ala Ser Glu Ser Val Ser Ala Thr Arg Ala Pro Phe Arg
            20                  25                  30

Leu Gly Ala Val Gly Ile Gly Ala Ile Ala Leu Val Val Leu Leu Ile
        35                  40                  45

Leu Phe Val Ile Ala Ile Pro Val Arg Asn Tyr Phe Gln Leu Arg Ser
    50                  55                  60

Asp Ile Ala Gln Thr Glu Ala Ser Ile Glu Ala Lys Glu Gln Gln Ile
65                  70                  75                  80

Lys Gln Leu Glu Ser Asp Leu Asn Arg Tyr Gln Ser Glu Ala Tyr Ile
                85                  90                  95

Arg Glu Gln Ala Arg Leu Arg Leu Gly Val Ile Glu Pro Gly Glu Thr
            100                 105                 110

Ala Phe Arg Ile Val Asp Pro Ala Leu Asp Thr Asp Thr Ser Val Thr
        115                 120                 125

Ser Asp Gly Asn Glu Glu Lys Pro Leu Gly Ala
    130                 135

<210> SEQ ID NO 6

<211> LENGTH: 543
<212> TYPE: DNA
<213> ORGANISM: Artificial Sequence
<220> FEATURE:
<223> OTHER INFORMATION: variant of pdz-ftsB

<400> SEQUENCE: 6

| | | | | | |
|---|---|---|---|---|---|
| atggcaaagc | agaagaaaac | tcataaaggc | cttgttcctg | tctcaagcag | ggaacgtgct | 60 |
| tcagagtcag | tttctgctac | ccgcgcccca | tttagattgg | gtgccgtcgg | catcggtgca | 120 |
| atcgcactcg | tagttcttct | catcctgttt | gtcatcgcga | ttcctgtgcg | taactatttt | 180 |
| cagctgcgct | ccgacatcgc | ccaaacagag | gcttccattg | aagccaaaga | acaacagatc | 240 |
| aaacaactgg | aatctgacct | caacaggtac | caatcagagg | cgtacatccg | cgaacaagca | 300 |
| cgcctgcgcc | taggcgtcat | tgaacctgga | gaaaccgcgt | tcagaatcgt | ggacccagca | 360 |
| ctagataccg | acacctcagt | cacctctgac | ggcaacgaag | agaaaccact | gggagcttga | 420 |
| tatgaaaacc | tctgggactc | agtcaccaag | ccagaagcac | tcggcgaaga | ggaaattgcg | 480 |
| cctccagcag | ttgagggaga | agttccaaca | cttgcaccaa | ctgaggaagc | aactgtgcaa | 540 |
| tag | | | | | | 543 |

<210> SEQ ID NO 7
<211> LENGTH: 33
<212> TYPE: DNA
<213> ORGANISM: Artificial Sequence
<220> FEATURE:
<223> OTHER INFORMATION: 0936F1 primer

<400> SEQUENCE: 7
gcaggtcgac tctagaccga ggacaccacc att        33

<210> SEQ ID NO 8
<211> LENGTH: 34
<212> TYPE: DNA
<213> ORGANISM: Artificial Sequence
<220> FEATURE:
<223> OTHER INFORMATION: 0936R1 primer

<400> SEQUENCE: 8
tctcaagcag ggaacgtgaa gaggaaattg cgcc        34

<210> SEQ ID NO 9
<211> LENGTH: 34
<212> TYPE: DNA
<213> ORGANISM: Artificial Sequence
<220> FEATURE:
<223> OTHER INFORMATION: 0936F2 primer

<400> SEQUENCE: 9
ggcgcaattt cctcttcacg ttccctgctt gaga        34

<210> SEQ ID NO 10
<211> LENGTH: 33
<212> TYPE: DNA
<213> ORGANISM: Artificial Sequence
<220> FEATURE:
<223> OTHER INFORMATION: 0936R2 primer

<400> SEQUENCE: 10
ccggggatcc tctagacggt ggaaaggcga tca        33

<210> SEQ ID NO 11
<211> LENGTH: 20

```
<212> TYPE: DNA
<213> ORGANISM: Artificial Sequence
<220> FEATURE:
<223> OTHER INFORMATION: 0936F3 primer

<400> SEQUENCE: 11
gggagcttga tatgaaaacc                                          20

<210> SEQ ID NO 12
<211> LENGTH: 20
<212> TYPE: DNA
<213> ORGANISM: Artificial Sequence
<220> FEATURE:
<223> OTHER INFORMATION: 0936R3 primer

<400> SEQUENCE: 12
ggttttcata tcaagctccc                                          20

<210> SEQ ID NO 13
<211> LENGTH: 17
<212> TYPE: DNA
<213> ORGANISM: Artificial Sequence
<220> FEATURE:
<223> OTHER INFORMATION: 0936F4 primer

<400> SEQUENCE: 13
aaccactggg agcttga                                             17

<210> SEQ ID NO 14
<211> LENGTH: 17
<212> TYPE: DNA
<213> ORGANISM: Artificial Sequence
<220> FEATURE:
<223> OTHER INFORMATION: 0936R4 primer

<400> SEQUENCE: 14
cggtggaaag gcgatca                                             17
```

CORYNEBACTERIUM MICROORGANISM WITH IMPROVED ABILITY TO PRODUCE L-LYSINE AND METHOD FOR PRODUCING L-LYSINE USING THE SAME

TECHNICAL FIELD

The present disclosure is related to a *Corynebacterium* microorganism with an improved ability to produce L-lysine and method for producing L-lysine using the same.

BACKGROUND ART

A microorganism of genus *Corynebacterium* is a gram positive bacteria and is widely used in the production of L-amino acid. L-amino acid, particularly, L-lysine, is used in animal feeds, medicines for humans, and cosmetic fields, and produced by fermentation using *Corynebacterium* strains.

There have been a number of attempts to improve a method of producing L-amino acid using *Corynebacterium* strains. Among the attempts, there has been research for improving *Corynebacterium* strains producing L-amino acids by disrupting or attenuating the expression of specific genes using recombinant DNA technology. In addition, there has been much research regarding the effects of amplifying genes related to biosynthesis of each L-amino acid on L-amino acid production and regarding improvement of *Corynebacterium* strains producing L-amino acids. Furthermore, exogenous genes derived from other bacteria may even be introduced.

However, there still is a need for strains with an improved ability to produce L-lysine beyond the conventional methods.

DETAILED DESCRIPTION OF THE INVENTION

Technical Problem

An aspect provides a coryneform microorganism with an improved ability to produce L-lysine.

Another aspect provides a method for producing L-lysine using the coryneform microorganism.

Technical Solution

An aspect provides a coryneform microorganism with an improved ability to produce L-lysine in which septum formation initiator protein is inactivated.

The term "septum formation initiator" as used herein refers to a factor that is necessary for initiating the formation of septum, i.e., a membranous structure that divides the inside of a cell during the cell division process of a coryneform microorganism. The cell division may occur in the presence of the septum formation initiator. In the presence of the septum formation initiator, the septum may be invaginated in the peripheral portion around the center of a cell to divide the cytoplasm into two. Synthesis of an outer membrane may occur thereafter, followed by cell division. The septum formation initiator protein may be one protein selected from Tables 1 and 2.

TABLE 1

| Entry | Entry name | Protein | Gene | Organism |
| --- | --- | --- | --- | --- |
| Q8NRS0 | Q8NRS0_CORGL | Septum formation factor and secretion protein | cg1112 Cgl0975 | *Corynebacterium glutamicum* (strain ATCC 13032/DSM 20300/JCM 1318/LMG 3730/NCIMB 10025) |
| G4QXS0 | G4QXS0_CORPS | Septum formation factor protein | Cp4202_0705 | *Corynebacterium pseudotuberculosis* 42/02-A |
| I3QWJ7 | I3QWJ7_CORPS | Septum formation factor protein | Cp258_0720 | *Corynebacterium pseudotuberculosis* 258 |
| I0DJM4 | I0DJM4_CORPS | Septum formation factor protein | Cp31_0721 | *Corynebacterium pseudotuberculosis* 31 |
| H2FRL0 | H2FRL0_CORPS | Septum formation factor protein | Cp3995_0727 | *Corynebacterium pseudotuberculosis* 3/99-5 |
| I4ASY7 | I4ASY7_CORPS | Septum formation factor protein | Cp162_0714 | *Corynebacterium pseudotuberculosis* Cp162 |
| I0ARP4 | I0ARP4_CORPS | Septum formation factor protein | Cp267_0749 | *Corynebacterium pseudotuberculosis* 267 |
| G4QUP8 | G4QUP8_CORPS | Septum formation factor protein | CpCIP5297_0731 | *Corynebacterium pseudotuberculosis* CIP 52.97 |
| G7U3I0 | G7U3I0_CORPS | Septum formation factor protein | Cp106_0699 | *Corynebacterium pseudotuberculosis* 1/06-A |
| G0I2E0 | G0I2E0_CORPS | Septum formation factor protein | CpPAT10_0713 | *Corynebacterium pseudotuberculosis* PAT10 |
| H6M3W9 | H6M3W9_CORPS | Septum formation factor protein | Cp316_0740 | *Corynebacterium pseudotuberculosis* 316 |
| H8LRF5 | H8LRF5_CORPS | Septum formation factor protein | CpP54B96_0726 | *Corynebacterium pseudotuberculosis* P54B96 |
| D9Q9H0 | D9Q9H0_CORP2 | Septum formation factor protein | CpC231_0714 | *Corynebacterium pseudotuberculosis* (strain C231) |
| E3F8E0 | E3F8E0_CORP9 | Septum formation factor protein | CpI19_0714 | *Corynebacterium pseudotuberculosis* (strain I19) |
| D9Q7G1 | D9Q7G1_CORP1 | Septum formation factor protein | Cp1002_0715 | *Corynebacterium pseudotuberculosis* (strain 1002) |

TABLE 2

| Entry | Entry name | Protein | Gene | Organism |
|---|---|---|---|---|
| C8NN43 | C8NN43_COREF | Septum formation factor and Secretion protein | HMPREF0290_1418 | Corynebacterium efficiens (strain DSM 44549/YS-314/AJ 12310/JCM 11189/NBRC 100395) |
| Q8FQS4 | Q8FQS4_COREF | Septum formation factor family protein | HMPREF0290_1417 | Corynebacterium efficiens (strain DSM 44549/YS-314/AJ 12310/JCM 11189/NBRC 100395) |
| E2S4T1 | E2S4T1_9CORY | Septum formation factor | HMPREF0305_11533 | Corynebacterium pseudogenitalium ATCC 33035 |
| E2S4T0 | E254T0_9CORY | Septum formation factor family protein | HMPREF0305_11532 | Corynebacterium pseudogenitalium ATCC 33035 |
| D7WEC6 | D7WEC6_9CORY | Septum formation factor | HMPREF0291_11160 | Corynebacterium pseudogenitalium ATCC 33030 |
| D7WEC7 | D7WEC7_9CORY | Septum formation factor family protein | HMPREF0291_11161 | Corynebacterium pseudogenitalium ATCC 33030 |
| E0MWT7 | E0MWT7_9CORY | Septum formation factor | HMPREF0277_0971 | Corynebacterium accolens ATCC 49726 |
| E0MWT8 | E0MWT8_9CORY | Septum formation factor family protein | HMPREF0277_0972 | Corynebacterium accolens ATCC 49726 |
| E2MWD5 | E2MWD5_9CORY | Septum formation factor and secretion protein | CORAM0001_0431 | Corynebacterium amycolatum SK46 |
| E0DIN5 | E0DIN5_9CORY | Septum formation factor | HMPREF0299_5548 | Corynebacterium matruchotii ATCC 14266 |
| G7HYM6 | G7HYM6_9CORY | Putative septum formation initiator | CCAS_08930 | Corynebacterium casei UCMA 3821 |
| C0XRQ5 | C0XRQ5_9CORY | Septum formation factor and secretion protein | HMPREF0298_1125 | Corynebacterium lipophiloflavum DSM 44291 |
| C6RB12 | C6RB12_9CORY | Septum formation factor and secretion protein | CORTU0001_0256 | Corynebacterium tuberculostearicum SK141 |
| C8RQC2 | C8RQC2_CORJE | Septum formation factor family protein | HMPREF0297_0224 | Corynebacterium jeikeium ATCC 43734 |
| D5UVG9 | D5UVG9_TSUPD | Septum formation factor | Tpau_3164 | Corynebacterium paurometabolum (strain ATCC 8368/DSM 20162/JCM 10117/NBRC 16120/NCTC 13040) (Tsukamurella paurometabola) |

The septum formation initiator may include a filamentous temperature sensitive (Fts) protein. The Fts protein is a protein that is involved in divisome formation, which may be necessary in the process of cell division of a microorganism. The Fts protein may include FtsB, FtsA, FtsZ, FtsEX, FtsK, FtsQ, FtsW, FtsI, or a combination thereof, specifically, FtsB. FtsB may have an amino acid sequence of SEQ ID NO: 1 or 70% homology thereof, specifically, 80% homology thereof, more specifically 90% homology thereof, most specifically 95% homology thereof. The term "homology" refers to the degree of identity between two amino acid sequences, which may be determined by using methods of utilizing BLAST 2.0 for calculating a parameter, such as score, identity, or similarity, which is widely known to those of ordinary skill in the art.

A gene encoding the Fts protein may be a nucleic acid encoding ftsA, ftsB, ftsZ, ftsEX, ftsK, ftsQ, ftsW, ftsI, or a combination thereof.

The ftsB gene involved in cell division of a coryneform microorganism may form divisome as well as ftsZ, ftsEX, ftsK, ftsQ, ftsW, and class B High Molecular Weight (HMW)-PBPs. The ftsB gene may be a nucleic acid encoding the amino acid sequence of SEQ ID NO: 1. The ftsB gene may be, e.g., an NCBI accession number NCgl0936 gene. The term "NCBI accession number NCgl0936 gene" refers to a gene having a nucleotide sequence of SEQ ID NO: 2 derived from Corynebacterium glutamicum strains. In addition, the gene may be present in microorganisms of genus Corynebacterium and producing substantially the same product as the NCBI accession number NCgl0936 gene does. The expression "substantially the same" as used herein means the same activity and control mechanism as those of the product of the NCBI accession number NCgl0936 gene.

The term "inactivation" as used herein means nonexhibition of a level of activity of cells or enzymes, which may be measured in the same type of cells or original enzymes comparable therewith. The same type of cells comparable therewith may be cells without being manipulated such as recombination or modification. In the microorganism, inactivation of a septum formation initiator protein may refer to being removed an activity of polypeptides, which encode the septum formation initiator. Further, in the microorganism, the septum formation initiator protein may be inactivated to a degree sufficient to produce L-lysine.

The inactivation may be caused by a recombination method. The recombination method may include homologous recombination method. The homologous recombination method may be performed by transforming a vector including a portion of sequences of the gene to a microorganism and culturing the microorganism in the presence of product of a selective marker, and thus the portion of sequences of the gene and the endogenous genes in the microorganism may undergo homologous recombination. The vector may be a pDZ-ΔftsB W140* vector including NCBI accession number NCgl0936 gene fragment represented by SEQ ID NO: 4 or a pDZ-ftsB W140* vector including NCBI accession NCgl0936 gene fragment represented by SEQ ID NO: 6. By the homologous recombination, the endogenous genes in the microorganism may be recombinated, and from among the recombinated genes, recombinants including the marker may be selected by the selective marker. By the homologous recombination method, a microorganism of genus Corynebacterium, in which an endogenous NCBI accession number NCgl0936 gene is inactivated, may be obtained.

In the microorganism, inactivation of protein activity may be caused by deletion, substitution, addition, inversion, or a combination thereof of a base, a nucleoside, a nucleotide, or a combination thereof of a gene. In detail, examples of a method of inactivating the protein activity may be gene knockout approach, antisense technology, or RNAi technology, The method of inactivating the protein activity may further include deletion of the initial copy of each gene, substituting the initial copy with a mutant, or expressing the initial copy from a weak promoter. In addition, substitution of a promoter of a gene encoding the protein, mutation transfer by random or site-directed mutagenesis, or gene disruption or knockout may also be used. Furthermore, methods of introducing unstable elements to mRNA or aberrating of ribosome-binding site (RBS) of RNA by gene modification may also be used.

Inactivation of genes may be achieved by transforming a vector including a portion of an NCBI accession number NCg10936 gene and a selective marker to a microorganism of genus *Corynebacterium*, followed by culturing in the presence of antibiotics and selecting.

The selective marker may be for selecting cells transformed with the vector. The selective marker may be a marker conferring a selectable phenotype, such as drug resistance, auxotrophy, cytotoxic drug resistance, or expression of surface proteins.

The coryneform microorganism may be selected from the group consisting of *Corynebacterium glutamicum, Corynebacterium ammoniagenes, Corynebacterium pseudotuberculosis, Corynebacterium efficiens, Corynebacterium pseudo genitalium, Corynebacterium genitalium, Corynebacterium accolens, Corynebacterium amycolatum, Corynebacterium matruchotii, Corynebacterium casei, Corynebacterium lipophiloflavum, Corynebacterium tuberculostearicum, Corynebacterium jeikeium, Corynebacterium paurometabolum*, and L-lysine producing mutants produced from a wild-type thereof. Specifically, the coryneform microorganism may be *Corynebacterium glutamicum*. The *Corynebacterium glutamicum* may be a *Corynebacterium glutamicum* with Accession No. KCCM11016P, KCCM10770P, KCCM11347P, or CJ3P.

The term "coryneform microorganism" as used herein refers to a microorganism of genus *Corynebacterium* with an ability to produce L-lysine. Examples of the coryneform microorganism may include a microorganism of genus *Corynebacterium* with an improved ability to produce L-lysine to which a mutation is introduced for inactivation of a gene encoding a septum formation initiator protein for the sake of improvement of the ability to produce L-lysine. The expression "with an/the ability to produce L-lysine" means, when the microorganism is cultured in medium, the microorganism has the capability of producing and secreting L-lysine in the medium. The coryneform microorganism may be a microorganism that may produce and accumulate L-lysine in a large amount in a culture medium, as compared with a wild-type thereof or a mother strain.

According to an embodiment, a gene encoding septum formation initiator protein e.g., FtsB in a coryneform microorganism is inactivated, thereby cell division of the coryneform microorganism may be inhibited, while the ability to produce L-lysine may be improved, relatively.

Another aspect provides a method for producing L-lysine, the method including culturing a microorganism according to the present invention so as to produce L-lysine in a culture medium; and recovering L-lysine from the microorganism or the culture medium. The microorganism is the same as described above.

Culturing the microorganism may be performed in a proper medium under culture conditions that are well known in the art. Such culturing process may be easily adjusted depending on a microorganism to be selected. The culturing method may include at least one selected from the group consisting of batch culture, continuous culture, and fed-batch culture.

The medium used in culturing may meet the requirements of a particular microorganism. The medium may be selected from the group consisting of carbon sources, nitrogen sources, trace elements, and a combination thereof.

The carbon source may be selected from the group consisting of carbohydrates, lipids, fatty acids, alcohols, organic acids, and a combination thereof. The carbohydrate may be glucose, sucrose, lactose, fructose, maltose, starch, cellulose, or a combination thereof. The lipid may be soybean oil, sunflower oil, castor oil, coconut oil, or a combination thereof. The fatty acid may be palmitic acid, stearic acid, linoleic acid, or a combination thereof. The alcohol may be glycerol or ethanol. The organic acid may include acetic acid.

The nitrogen source may include an organic nitrogen source, an inorganic nitrogen source, or a combination thereof. The organic nitrogen source may be selected from the group consisting of peptone, yeast extract, meat extract, malt extract, corn steep liquid (CSL), soybean meal, and a combination thereof. The inorganic nitrogen source may be selected from the group consisting of urea, ammonium sulfate, ammonium chloride, ammonium phosphate, ammonium carbonate, ammonium nitrate, and a combination thereof.

The medium may include one selected from the group consisting of phosphorous, metal salts, amino acids, vitamins, precursors, and a combination thereof. The phosphorous source may include potassium dihydrogen phosphate, dipotassium phosphate, and a sodium-containing salt corresponding thereto. The metal salt may be magnesium sulfate and iron sulfate.

The medium or individual components may be added to the culture medium in a batch culture, a continuous culture, or a fed-batch culture.

In the culturing method, the pH of the culture may be adjusted. The pH adjustment may be performed by adding ammonium hydroxide, potassium hydroxide, ammonia, phosphoric acid, or sulfuric acid to the culture. Further, the culturing method may include prevention of air bubbles generation. The prevention of air bubbles generation may be performed by using an antifoaming agent. The antifoaming agent may include fatty acid polyglycol ester. Further, the culturing method may include injection of gas into the culture. The gas may include any gas to maintain the aerobic condition of the culture. The gas may be oxygen or oxygen-containing gas. The oxygen-containing gas may include air. In the culturing, the temperature of the culture may be in a range of 20 to 45° C., for example, 22 to 42° C., or 25 to 40°

C. The culturing may be continued until the production of L-lysine reaches a desired level.

In a method according to the present invention, culturing may be continuous culturing or batch culturing, such as batch, fed-batch, and repeated fed-batch cultures. Such a culturing method is well-known in the art, and any suitable method may be used. The L-amino acid may be separated and analyzed by anion exchange chromatography and ninhydrin derivatization.

Advantageous Effects of the Application

According to a microorganism, in which a gene encoding a septum formation initiator protein is inactivated, according to an aspect, an ability to produce L-lysine of the microorganism may be improved.

According to a method for producing L-lysine according to an aspect, L-lysine may be produced with high productivity.

Mode Of The Invention

Hereinafter, the present invention will be described in more detail with reference to Examples. However, these Examples are for illustrative purposes only, and the scope of the present invention is not intended to be limited by these Examples.

EXAMPLE 1

Preparation of ftsB gene-inactivated Recombinant Vector by Deletion

The sequence of nucleotides of an ftsB gene (SEQ ID NO: 2) was obtained, based on the base sequence in the GenBank of US National Institute of Health (NIH Genbank). In order to make a gene fragment in which the open reading frame of ftsB internally disappeared, based on SEQ ID NO: 2, primers 0936F1, 09369R1, 0936F2, and 0936R2 were constructed and called SEQ ID NOs: 7 to 10, respectively.

In order to prepare an inactivated recombinant vector due to ftsB gene deletion, a pDZ vector (refer to Korea Patent Registration No. 10-0924065) was used. Then, as described above, nucleic acid molecules constructed for inactivation, having the modified sequence of the ftsB gene, were inserted into a multi-cloning site of the pDZ vector, thus preparing a pDZ-ΔftsB vector including a nucleic acid sequence of SEQ ID NO: 4. The nucleic acid sequence of SEQ ID NO: 4 encodes an amino acid having an amino acid sequence of SEQ ID NO: 3.

PCR was performed using *Corynebacterium glutamicum* ATCC13032 genome DNA as a template and using the primers 0936F1-0936R1 and 0936F2-0936R2. PfuUltra™ high-fidelity DNA polymerase (Stratagene) was used as a polymerase. PCR conditions were as follows; denaturation at 96° C. for 30 seconds, annealing at 58° C. for 30 seconds, polymerization at 72° C. for 2 minutes, and 30 cycles.

As a result, a pair of ftsB-A and ftsB-B DNA fragments were obtained, each including ftsB gene of 74 by and 95 bp, respectively. The amplified products were cloned into the pDZ vector using Infusion cloning kit (Invitrogen), resulting in the construction of a pDZ-ΔftsB vector. The pDZ-ΔftsB vector includes the both XbaI terminus of 135 by ftsB and a fragment without 408 by internal region of ftsB.

EXAMPLE 2

Preparation of ftsB Gene-inactivated Recombinant Vector by Introduction of Stop Codon In order to prepare an ftsB gene-inactivated recombinant vector by introduction of a stop codon, a pDZ vector was used, and a primer was constructed to substitute the anticodon of the 140$^{th}$ amino acid in the open reading frame of ftsB gene, i.e., tryptophan, with a stop codon. Using a pair of primers 0936 F1 and 0936 R3 and a pair of primers 0936 F3 and 0936R2, PCR for amplification was performed in the same manner as in Example 1, and the amplified products cloned into a pDZ vector, resulting in the construction a pDZ-ftsB W140* vector. The sequences of the pair of primers 0936F3 and 0936R3 were indicated as SEQ ID NO: 11 and 12, respectively. The sequence of the amino acids of the fts gene cloned into the constructed vector was SEQ ID NO: 5, and the sequence of the nucleic acids thereof was SEQ ID NO: 6 (nucleotide sequence).

EXAMPLE 3

Construction of ftsB Gene-inactivated Strain

The L-lysine production strain *Corynebacterium glutamicum* KCCM11016P (the (old) Accession number KFCC10881, refer to Korea Patent Registration No. 10-0159812 and 10-0397322) was transformed with the recombinant vectors constructed in Examples 1 and 2 by an electric pulse method (using the transformation method of Appl. Microbiol. Biotechnol. (1999) 52:541-545). Then, the strain having the target gene inserted by gene homology on the chromosome was selected from the selection medium containing 25 mg/L of kanamycin. The successful insertion of the vector in the chromosome was confirmed by observing if the colony was blue on the solid medium containing X-gal (5-bromo-4-chloro-3-indolyl-β-D-galactoside). The primary chromosome inserted strain was shaking-cultured in a nutrient medium (at a temperature of 30° C. for 8 hours), which was then diluted from $10^{-4}$ to $10^{31\ 10}$, followed by smearing on the solid medium containing X-gal. While most colonies were blue, there were some colonies that were white. Those low rate white colonies were selected, which proceeded to the selection of the strain in which the ftsB gene was inactivated by the secondary crossover.

In order to select the strain in which the ftsB gene was inactivated by deletion, a pair of gene-specific primers, SEQ ID NO: 7 and SEQ ID NO: 10, 0936F1-0936R2 were used as primers to perform PCR. The base sequence regarding a target site was analyzed for final confirmation, resulting in the construction of inactivated strain KCCM11016P-ΔftsB due to deletion of ftsB gene. In order to select the strain in which the ftsB gene inactivated due to transfer of modified stop codon, a pair of primers, SEQ ID NO: 7 and SEQ ID NO: 10, 0936F1-0936R2 were used as primers to perform PCR. The base sequence regarding a target site was analyzed for final confirmation, resulting in the construction of ftsB gene-inactivated strain KCCM11016P-ftsB W140* due to introduction of a stop codon.

To examine the effects in other strains belonging to the genus *Corynebacterium glutamicum*, using KCCM10770P (refer to Korea Patent Registration No. 10-0924065), KCCM11347P (refer to Korea Patent Registration No. 10-1994-0001307) and CJ3P (Binder et al. Genome Biology 2012, 13:R40) as mother strains, ftsB gene-deleted strains and stop codon-introduced strains, i.e., KCCM10770P-ΔftsB, KCCM11016P-ftsB W140*, KCCM11347P-ΔftsB, KCCM11347P-ftsB W140*, CJ3P-ΔftsB, CJ3P-ftsB W140*, were constructed in the same manner as in the above method.

EXAMPLE 4

L-lysine Production in ftsB Gene-inactivated Strain

The L-lysine production strain *Corynebacterium glutamicum* KCCM11016P-ΔftsB, KCCM11016P-ftsB W140*, KCCM10770P-ΔftsB, KCCM10770P-ftsB W140*, KCCM11347P-ΔftsB, KCCM11347P-ftsB W140*, CJ3P-ΔftsB, and CJ3P-ftsB W140* constructed in Example 3 were cultured for L-lysine production, as in the following method.

The *Corynebacterium glutamicum* mother strain and KCCM11016P-ΔftsB, KCCM11016P-ftsB W140*, KCCM10770P-ΔftsB, KCCM10770P-ftsB W140*, KCCM11347P-ΔftsB, KCCM11347P-ftsB W140*, CJ3P-ΔftsB, and CJ3P-ftsB W140* were each inoculated in a 250 ml corner-baffled flask containing 25 ml of seed culture medium, followed by shaking-culture at 30° C. for 20 hours with 200 revolutions per minute (rpm). Then, 1 ml of each of the seed culture media was inoculated in a 250 ml corner-baffled flask containing 24 ml of production medium, followed by shaking-culture at 30° C. for 120 hours with 200 rpm. The compositions of the seed culture medium and the production medium are as follows.

Seed Culture Medium (pH 7.0)

raw sugar 20 g, pepton 10 g, yeast extract 5 g, urea 1.5 g, $KH_2PO_4$ 4 g, $K_2HPO_4$ 8 g, $MgSO_4$ $7H_2O$ 0.5 g, biotin 100 μg, thiamine HCl 1000 μg, calcium-pantothenate 2000 μg, nicotinamide 2000 μg (in distilled water 1 L)

Production Medium (pH 7.0)

glucose 100 g, $(NH_4)_2SO_4$ 40 g, soybean protein 2.5 g, corn steep solids 5 g, urea 3 g, $KH_2PO_4$ 1 g, $MgSO_4$ $7H_2O$ 0.5 g, biotin 100 μg, thiamine hydrochloride 1000 μg, calcium-pantothenate 2000 μg, nicotinamide 3000 μg, $CaCO_3$ 30 g (in distilled water 1 L)

Upon completion of the culture, L-lysine production was measured by the method using HPLC. The concentrations of L-lysine in culture solutions of *Corynebacterium glutamicum* mother strain and KCCM11016P-ΔftsB, KCCM11016P-ftsB W140*, KCCM10770P-ΔftsB, KCCM10770P-ftsB W140*, KCCM11347P-ΔftsB, KCCM11347P-ftsB W140, CJ3P-ΔftsB, and CJ3P-ftsB W140* are shown in Table 3. The results shown in Table 3 are the average value by repetitive experiment.

TABLE 3

|  | Lysine (g/L) | | | OD 560 nm | | |
| --- | --- | --- | --- | --- | --- | --- |
|  | Batch 1 | Batch 2 | Batch 3 | Batch 1 | Batch 2 | Batch 3 |
| KCCM11016P | 43.3 | 44.6 | 43 | 54.7 | 57.5 | 55 |
| KCCM11016P-Δ ftsB | 44.9 | 45 | 46 | 53 | 53.4 | 52.5 |
| KCCM11016P-ftsB W140* | 44.5 | 45 | 46.1 | 51.9 | 52 | 52.6 |
| KCCM10770P | 46.9 | 47 | 47.3 | 50.5 | 51 | 52 |
| KCCM10770P-Δ ftsB | 48.9 | 48.5 | 48.4 | 48.6 | 49 | 48 |
| KCCM10770P-ftsB W140* | 48 | 48.2 | 48.9 | 48.1 | 48.5 | 49 |
| KCCM11347P | 38 | 37.7 | 38.5 | 79 | 80 | 81 |
| KFCC10750-Δ ftsB | 39.5 | 39 | 39.8 | 76 | 75 | 75 |
| KCCM11347P-ftsB W140* | 40 | 39.5 | 39.4 | 74 | 76 | 75 |
| CJ3P | 8.5 | 8 | 8 | 102 | 105 | 103 |
| CJ3P-Δ ftsB | 9.1 | 9.6 | 9 | 97 | 96.5 | 97.2 |
| CJ3P-ftsB W140* | 9.2 | 9 | 9.5 | 98 | 97.5 | 97.7 |

As shown in Table 3, when an ftsB gene was deleted or a stop codon was introduced in the mother strain KCCM11016P, the lysine production increased by about 4% in all of them. These results indicate that the concentration of lysine increased not by the structural changes of the ftsB gene itself but by the deletion of FtsB protein that is a septum formation initiator. In addition, the concentrations of lysine of the FtsB inactivated strains from other mother strains, KCCM10770P, KCCM11347P, and CJ3P, increased by about 4%, as compared with the mother strains having wild-type FtsB activity. On the other hand, the cell volume of the FtsB inactivated strains was decreased by about 5%, as compared with the mother strains. This result implies that an ability to produce lysine may be improved by controlling the amount of strains due to suppression of cell division of lysine production strains. KCCM11016P-ftsB W140* (CA01-2274) was deposited at Korean Culture Center of Microorganisms, located at Urim bd., Hongje-1-dong, Seodaemun-gu, Seoul, Korea on Sep. 27, 2013 under the Accession number KCCM11454P.

Depository authority: Korean Culture Center of Microorganisms (international)
Accession number: KCCM 11454P
Accession date: Sep. 27, 2013

The invention claimed is:

1. A Coryneform microorganism with an improved ability to produce L-lysine in which a septum formation initiator protein is inactivated, wherein the septum formation initiator protein is a filamentous temperature sensitive B (FtsB) protein.

2. The microorganism according to claim 1, wherein the septum formation initiator protein has the amino acid sequence of SEQ ID NO: 1.

3. The microorganism according to claim 1, wherein the Coryneform microorganism is *Corynebacterium glutamicum*.

4. A method for producing L-lysine, the method comprising:
    culturing the microorganism of claim 1, to produce L-lysine in a culture medium; and
    recovering L-lysine from the microorganism or the culture medium.

* * * * *